United States Patent
Morizono et al.

(10) Patent No.: US 7,105,512 B2
(45) Date of Patent: Sep. 12, 2006

(54) OPHTHALMIC AQUEOUS PHARMACEUTICAL PREPARATION

(75) Inventors: Daisuke Morizono, Tokyo (JP); Hidekazu Suzuki, Tokyo (JP); Masanobu Takeuchi, Tokyo (JP); Kenji Naito, Tokyo (JP)

(73) Assignee: Wakamoto Pharmaceutical Co., Ltd., Tokyo (JP)

( * ) Notice: Subject to any disclaimer, the term of this patent is extended or adjusted under 35 U.S.C. 154(b) by 51 days.

(21) Appl. No.: 10/153,632

(22) Filed: May 24, 2002

(65) Prior Publication Data

US 2003/0055051 A1    Mar. 20, 2003

(30) Foreign Application Priority Data

Nov. 24, 1999  (JP) ................................ 11-333166
Nov. 24, 1999  (JP) ................................ 11-333167
Jan. 31, 2000  (JP) ............................. 2000-021296

(51) Int. Cl.
*A61K 31/54* (2006.01)
(52) U.S. Cl. .................... 514/226.5; 514/669; 514/912
(58) Field of Classification Search ............. 514/226.5, 514/912, 669
See application file for complete search history.

(56) References Cited

U.S. PATENT DOCUMENTS 4,829,088 A * 5/1989 Doulakas .................... 514/567

FOREIGN PATENT DOCUMENTS

| EP | 1173661 | 12/1969 |
|---|---|---|
| EP | 0 390 071 | 10/1990 |
| EP | 0 945 134 | 9/1999 |
| JP | 54-92976 | 7/1979 |
| JP | 56-73023 | 6/1981 |
| WO | WO 93/01814 | * 2/1993 |
| WO | WO 99/01814 | 2/1993 |
| WO | WO 99/09988 | 3/1993 |
| WO | WO 99/59634 | 11/1999 |

OTHER PUBLICATIONS

The Merch Index, Eleventh Edition, 1989.*
Derwent Abstract 1993-058509, 200161 (1993).*

* cited by examiner

*Primary Examiner*—Zohreh Fay
(74) *Attorney, Agent, or Firm*—Oblon, Spivak, McClelland, Maier & Neustadt, P.C.

(57) ABSTRACT

The present invention provides an ophthalmic aqueous pharmaceutical preparation, which is excellent in anti-inflammatory effect, which is less stimulative and which has high safety and excellent storage stability. The ophthalmic aqueous pharmaceutical preparation comprises meloxicam and trometamol.

7 Claims, No Drawings

OPHTHALMIC AQUEOUS PHARMACEUTICAL PREPARATION

FIELD OF THE INVENTION

The present invention relates to an ophthalmic aqueous pharmaceutical preparation, which has an excellent anti-inflammatory effect, which is less irritant, which has high safety and which is excellent in the storage stability.

BACKGROUND ART

It has been known that meloxicam shows a cyclooxygenase-2-selective anti-inflammatory effect. A non-steroidal anti-inflammatory drug containing meloxicam as an effective component has presently been put on the market as a therapeutic agent for inflammatory diseases and rheumatism, in the form of drugs for internal use and parenteral injections.

It has been reported that if meloxicam is used in the ophthalmic application, it shows a strong anti-inflammatory effect and it also shows a low probability of damaging corneal epithelial cells or the conjunctival cells as compared with the conventional cyclooxygenase-1- and cyclooxygenase-2-nonselective non-steroidal anti-inflammatory agents (International Patent Application Serial No. PCT/JP99/02522).

Moreover, an ophthalmic pharmaceutical preparation containing meloxicam as an effective component is a non-steroidal anti-inflammatory agent and therefore, it would be expected that the pharmaceutical preparation could be used in the treatment of wide variety of diseases such as conjunctivitis, blepharitis, corneitis, scleritis, episcleritis, anterior (ophthalmic) uveitis and post-operative inflammation.

There have been known an ointment, a gel and an eye drop as dosage forms of the ophthalmic pharmaceutical preparation and the eye drop may further be divided into a suspension type pharmaceutical preparation and an aqueous solution type pharmaceutical preparation. The eye drop may easily be administered and therefore, it has widely been used, but the suspension type pharmaceutical preparation suffers from various problems such as uncomfortable feeling with foreign substances (or suspensoids) upon the administration thereof, the scattering of dose and the adhesion of the suspended matter or suspensoids to the container of the suspension. Contrary to this, the aqueous solution type pharmaceutical preparation never suffers from such problems associated with the suspension type one and it is advantageous in that the drug concentration is substantially constant or uniform and that the drug component may easily diffuse upon the administration thereof.

To use a certain drug in the form of an aqueous solution type pharmaceutical preparation (hereunder simply referred to as "aqueous solution"), the drug should be dissolved in water. Therefore, in case where meloxicam is used in the form of an aqueous solution, it is likewise necessary to dissolve A meloxicam in water. However, meloxicam has quite poor solubility in water. More specifically, meloxicam is slightly soluble in an alkaline aqueous solution, but it has a very low solubility in water at an almost neutral pH value.

It has in general been recognized that the pH value of the eye drop preferably ranges from 5 to 9 since it may give a stimulus to the eye (Monthly Ophthalmic Diagnostic Practice, "42. How to Use Eye Drops", published on Jan. 1, 1999). However, meloxicam could not be dissolved in water at an approximately physiological pH value to a concentration sufficient for ensuring the efficacy thereof.

To use a certain drug in the form of an aqueous solution, not only the drug should be dissolved in water to a concentration sufficient for ensuring the efficacy thereof, but also one should pay close attention to reduce the stimulus to a patient to the lowest possible level since the eye is quite susceptible for stimuli. In addition, the resulting aqueous solution should be excellent in safety and storage stability.

In case where an aqueous solution is prepared using meloxicam as an effective component, the foregoing requirements should likewise be satisfied, but there has not yet been known any conventional report, which can provide any useful suggestion for solving the foregoing problem.

As a method for dissolving meloxicam in water, there has been known a means for forming a salt of meloxicam with meglumine (N-methyl-D-glucamine salt) (Japanese Un-Examined Patent Publication (hereunder referred to as "J.P. KOKAI") No. Sho 54-92976). However, the meglumine salt of meloxicam suffers from such problems that it has considerably low solubility in water and that if the amount thereof dissolved in water is increased, the pH value of the resulting solution abruptly increases to such an extent that the pH value is beyond the preferred range of from 5 to 9. In fact, the inventors of this invention have tried to prepare an aqueous solution of meloxicam using meglumine, but it has been proved that only a small amount of meloxicam is dissolved in water and the pH value of the resulting aqueous solution is higher than the neutral range or higher than 9.0 and this requires the control of the pH value of the aqueous solution prior to practical use.

In the commercially available injection containing meloxicam, the meloxicam is dissolved using poloxamer as a surfactant and meglumine. This pharmaceutical preparation is excellent in the ability of solubilizing meloxicam as compared with the pharmaceutical preparation in which meloxicam is dissolved simply using meglumine (J.P. KOKAI No. Sho 54-92976), but the former is not preferred from the viewpoint of safety since it comprises a large amount of a surfactant, which may have a probability of causing hemolysis and of damaging cells.

International Publication No. WO99/09988 discloses an ophthalmic aqueous gel in which meloxicam is dissolved using $\beta$-cyclodextrin. The tissue-transfer ability of the drug, which is dissolved in water through the formation of a clathlate compound with $\beta$-cyclodextrin is dependent on the strength of the bond of the drug with the $\beta$-cyclodextrin and accordingly, it has been pointed out that the bioavailability of the drug included in the eye drop, which makes use of $\beta$-cyclodextrin as a solubilizing agent, is low as compared with the commonly used eye drop. In addition, the gel suffers from a problem such that it is limited in the applications, as compared with the eye drop.

As has been discussed above in detail, it is very difficult to prepare an aqueous pharmaceutical preparation or a solution comprising meloxicam as an effective component, which is less stimulative to a patient and has high safety and excellent storage stability. For this reason, there has not yet been put on the market any ophthalmic aqueous pharmaceutical preparation containing meloxicam as an effective component.

SUMMARY OF THE INVENTION

In view of the present status detailed above, it is an object of the present invention to provide an ophthalmic aqueous pharmaceutical preparation, which has an excellent anti-inflammatory effect, which is less stimulative to a patient, which has high safety and which is excellent in the storage stability.

According to the present invention, there is thus provided an ophthalmic aqueous pharmaceutical preparation comprising meloxicam and trometamol.

In the aqueous pharmaceutical preparation of the present invention, the concentration of meloxicam preferably ranges from 0.01 to 6% (w/v), while the molar concentration of trometamol is preferably 1.7 to 100 times that of meloxicam. More preferably, the concentration of meloxicam ranges from 0.7 to 3% (w/v), while that of trometamol ranges from 0.48 to 6% (w/v).

In the aqueous pharmaceutical preparation of the present invention, the pH value is preferably ranges from 7 to 9.

The ophthalmic aqueous pharmaceutical preparation of the present invention can be prepared by dissolving meloxicam in an aqueous solution of trometamol at a high temperature. The temperature of the hot aqueous trometamol solution preferably ranges from 70 to 100° C.

According to another aspect of the present invention, there is also provided a compound represented by the following Formula (2):

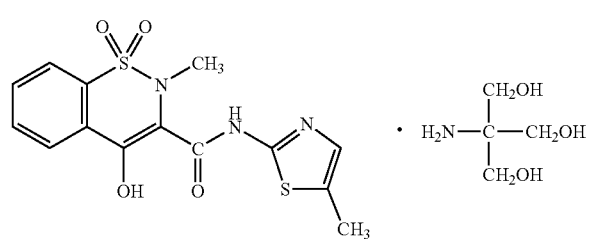

According to a further aspect of the present invention, there is provided an ophthalmic aqueous pharmaceutical preparation containing the compound of Formula (2) as an effective component.

DETAILED DESCRIPTION OF THE INVENTION

The present invention will hereunder be described in more detail.

The ophthalmic aqueous pharmaceutical preparation of the present invention comprises meloxicam and trometamol.

The meloxicam used in the present invention is a compound represented by the following Formula (1) and shows a cyclooxygenase-2-selective anti-inflammatory effect:

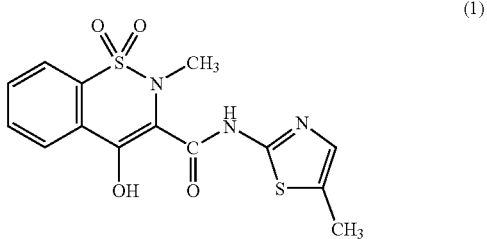

If meloxicam is used in an ophthalmic agent, it shows an excellent anti-inflammatory effect and it also has a low probability of damaging corneal epithelial cells or conjunctival cells.

The solubility of meloxicam in water (at 25° C.) near the neutral pH region is very low on the order of about 0.2 mg/100 mL as expressed in terms of the saturated concentration, which is insufficient for the preparation of an aqueous pharmaceutical preparation containing the same. For this reason, any aqueous pharmaceutical preparation cannot be obtained by simply adding meloxicam to water.

In the ophthalmic aqueous pharmaceutical preparation according to the present invention, the concentration of meloxicam is not restricted to any specific range inasmuch as the resulting preparation would ensure the desired drug efficacy and the concentration falls within the range required for the preparation of such an intended ophthalmic aqueous pharmaceutical preparation, but it preferably ranges from 0.01 to 6% (w/v). This is because if the meloxicam concentration is less than 0.01% (w/v), any desired efficacy cannot be expected, while if it exceeds 6% (w/v), it is difficult to completely dissolve meloxicam even in an aqueous trometamol solution at a high temperature. The meloxicam concentration more preferably ranges from 0.7 to 3% (w/v).

The trometamol used in the present invention may be its free state or pharmaceutically acceptable salts thereof. Examples of pharmaceutically acceptable salts of trometamol are hydrochloride, maleic acid salt and phosphoric acid salts thereof.

Wako Pure Chemical Industry Co. Ltd., Kanto Chemical Co. Ltd. and Sigma Aldrich Japan Co. Ltd. manufacture and sell the foregoing trometamols and thus they may easily commercially be available from these companies.

Trometamol has commonly been used as a buffering agent. The use of trometamol as a solubilizing agent is disclosed in the following G.B. Patent No. 1,173,661 and J.P. KOKAI No. Sho 56-73023, but both of these patents never refer to meloxicam.

G.B. Patent No. 1,173,661 discloses a method for dissolving an organic mercury compound in water comprising adding an organic mercury compound and an equimolar amount of trometamol to water and admixing them at room temperature. This article also discloses that the addition of trometamol in an amount higher than the equimolar amount never distinctly improves the solubility of the organic mercury compound. This article never refers to meloxicam.

J.P. KOKAI No. Sho 56-73023 discloses the use of trometamol for solubilizing, in water, a non-steroidal anti-inflammatory agent carrying one or at least two hydrophobic side chains and a carboxyl group. However, this article never refers to meloxicam as well.

In the present invention, the use of trometamol would permit the solubilization of hardly water-soluble meloxicam in water to a concentration sufficient for ensuring the desired efficacy thereof. Moreover, the use of trometamol as a solubilizing agent would permit the control of the pH value of the resulting aqueous pharmaceutical preparation to such a level that it falls within the neutral range and thus permits the preparation of an ophthalmic aqueous pharmaceutical preparation, which hardly stimulates the eye, which is excellent in safety and which has excellent storage stability.

As has been discussed above, it has already been known to use meglumine as a meloxicam-solubilizing agent, but the solubility of the resulting meglumine salt of meloxicam is not satisfactorily high and the meloxicam concentration thus achieved is insufficient in some applications. Moreover, a further increase of the amount thereof dissolved results in an abrupt increase of the pH value of the resulting solution even to a level, which is beyond the pH range of from 5 to 9 preferred for the ophthalmic aqueous pharmaceutical preparation or a level of higher than 9.0. This is not preferred from the viewpoint of stimulation and safety.

The foregoing concentration of trometamol is preferably 1.7 to 100 times that of meloxicam as expressed in terms of the molar concentration. If the former is less than 1.7 times that of the latter, it is difficult to sufficiently dissolve meloxicam, while if it exceeds 100 times, trometamol is added to the pharmaceutical preparation in an amount higher than that required for the dissolution of meloxicam and this in turn leads to an increase of the osmotic pressure of the resulting preparation and an increase of the stimulation experienced when the preparation is practically applied to the eyes. In addition, the use of trometamol in excess is not preferred from the economical standpoint.

If the concentration of meloxicam falls within the range of from 0.7 to 3% (w/v), that of trometamol preferably ranges from 0.48 to 6% (w/v). The use of trometamol in an amount ranging from 0.48 to 6% (w/v) would permit the complete dissolution of meloxicam to give a pharmaceutical preparation having a meloxicam concentration ranging from 0.7 to 3% (w/v).

The ophthalmic aqueous pharmaceutical preparation of the present invention may comprise trometamol salt of meloxicam. The trometamol salt of meloxicam is a novel compound whose physical properties are for the first time elucidated by the inventors of this invention and this constitutes an aspect of the present invention.

The trometamol salt of meloxicam is a compound represented by the following Formula (2):

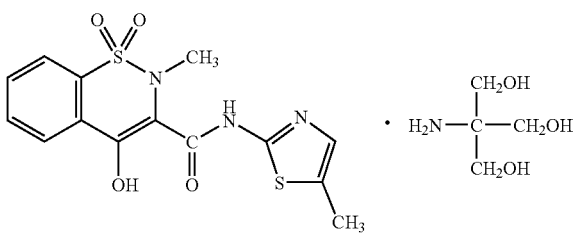

The ophthalmic aqueous pharmaceutical preparation of the present invention comprises meloxicam and trometamol. In this respect, if meloxicam and trometamol are present in the form of the compound represented by Formula (2) in the aqueous pharmaceutical preparation, the concentration of the compound of Formula (2) preferably ranges from 0.1 to 50 mg/mL. This is because if the concentration is less than 0.1 mg/mL, the resulting preparation has insufficient drug efficacy, while if it exceeds 50 mg/mL, crystals of meloxicam are easily separated from the preparation when it is stored at a low temperature.

The ophthalmic aqueous pharmaceutical preparation of the present invention can be prepared by dissolving meloxicam in an aqueous trometamol solution at a high temperature.

Meloxicam is less soluble in water. Surprisingly, however, it is highly soluble in an aqueous trometamol solution at a high temperature. In this case, the solubility of meloxicam in water is significantly high as compared with that observed when meloxicam is dissolved in water using meglumine. Meloxicam once dissolved in an aqueous trometamol solution at a high temperature is never separated from the resulting meloxicam-containing aqueous solution even when the temperature of the solution is lowered to room temperature. For this reason, the resulting ophthalmic aqueous pharmaceutical preparation has a concentration sufficient for ensuring the desired drug efficacy and is excellent in the storage stability.

There have conventionally been used such a means for dissolving a hardly soluble drug in water as the formation of a salt and the use of a surfactant, but there has never been tried to use any method, which makes use of hot water. Therefore, the method for dissolving a hardly soluble drug in water using hot water can be considered to be a quite unique one. The foregoing G.B. Patent No. 1,173,661 and J.P. KOKAI No. Sho 56-73023 never disclose or suggest the fact that an aqueous trometamol solution at a high temperature may serve as a strong solubilizing agent for meloxicam.

The foregoing hot aqueous trometamol solution preferably has a temperature ranging from 70 to 100° C. If the temperature of the aqueous solution is not less than 70° C., meloxicam can completely be dissolved in water.

The method for preparing the foregoing hot trometamol aqueous solution may comprise the steps of, for instance, heating water and then dissolving trometamol therein; or dissolving trometamol in water and then heating the resulting trometamol aqueous solution.

Other drugs hardly soluble in water may be dissolved in water using an aqueous trometamol solution at a high temperature, like meloxicam.

Examples of other hardly soluble drugs are isoxicam, piroxicam, tenoxicam and pharmaceutically acceptable salts thereof.

The pH value of the ophthalmic aqueous pharmaceutical preparation of the present invention preferably ranges from 7 to 9. If the pH value thereof falls within the range of from 7 to 9, the stimulation to the eyes upon the administration of the preparation can sufficiently be reduced. The pH value thereof more preferably ranges from 7.0 to 8.4.

The ophthalmic aqueous pharmaceutical preparation of the present invention may, if necessary and appropriately, comprise other additives inasmuch as they never impair the desired effects of the preparation and examples of such additives are other pH-adjusting agents, solubilizing agents, stabilizing agents, preservatives, isotonizing agent, thickening agents and/or surfactants.

Specific examples of the foregoing pH-adjusting agents are acids such as ascorbic acid, hydrochloric acid, gluconic acid, acetic acid, lactic acid, boric acid, phosphoric acid compounds such as monosodium phosphate and sodium hydrogen phosphate, sulfuric acid, tartaric acid and citric acid; bases such as potassium hydroxide, calcium hydroxide, sodium hydroxide and magnesium hydroxide, monoethanolamine, diethanolamine and triethanolamine, and amino acids such as glycine, histidine and ε-aminocaproic acid.

The foregoing solubilizing agent is not restricted to any particular one and examples thereof include polysorbate, propylene glycol and polyvinyl pyrrolidone.

The foregoing stabilizing agent is not likewise limited to any specific one and examples thereof are sodium hydrogen sulfite, glycerin, sodium citrate, butyl hydroxyanisole, benzalkonium chloride, edetic acid and pharmaceutically acceptable salts thereof, tocopherol and derivatives thereof, with sodium edetate being preferably used because of its excellent pigmentation-inhibitory effect, pH-stabilization effect and ability of maintaining high activity of effective components.

The foregoing preservative is not limited to any specific one and specific examples thereof include reversed soap such as benzalkonium chloride, benzethonium chloride and gluconic acid chlorhexidine; parabens such as methyl p-hydroxybenzoate, propyl p-hydroxybenzoate and butyl p-hydroxybenzoate; alcohols such as chlorobutanol, phenylethyl alcohol and benzyl alcohol; organic acid and salts thereof such as sodium dehydroacetate, sorbic acid and potassium sorbate; and organic mercury-containing compound such as thimerosal.

The foregoing isotonizing agent is not restricted to any specific one and specific-examples thereof are sodium chloride, potassium chloride, D-mannitol, glucose, glycerin, xylitol and propylene. Among these, D-mannitol is used as a preferred isotonizing agent because of its excellent pigmentation-inhibitory effect, pH-stabilization effect and ability of maintaining high activity of effective components. In this respect, however, these effects never show any dependency on the D-mannitol concentration and therefore, it is more preferred to use the same at a concentration at which the osmotic pressure is equal to that of the physiological saline.

The thickening agent listed above is not likewise restricted to any particular one and specific examples thereof are methylcellulose, ethyl cellulose, hydroxypropyl methylcellulose, polyvinyl pyrrolidone, polyvinyl alcohol, sodium chondroitin sulfate, sodium hyaluronate and chitosan.

The foregoing surfactant is not restricted to any specific one and may be, for instance, polysorbate and polyoxyethylene-hardened castor oil.

Diseases to which the ophthalmic aqueous pharmaceutical preparation of the present invention can be applied are not restricted to particular ones inasmuch as they are accompanied by the inflammation of the eyes and examples thereof are conjunctivitis, blepharitis, corneitis, scleritis, episcleritis, anterior (ophthalmic) uveitis and post-operative inflammation.

The ophthalmic aqueous pharmaceutical preparation of the present invention may be charged in a plastic eye drop bottle and then used as an eye drop.

The dose of the ophthalmic aqueous pharmaceutical preparation of the present invention is appropriately selected depending on various factors such as the symptoms to be treated and the age of each particular patient and each dosage form. If the pharmaceutical preparation of the invention is used as an eye drop and the eye drop comprises, for instance, meloxicam in an amount ranging from 0.01 to 6% (w/v), however, it is sufficient to drop the same in the eyes one to several times a day.

The dosage form of the ophthalmic aqueous pharmaceutical preparation of the present invention is not restricted to an eye drop, but may be an orally administered agent and an injection, or may be used in drugs other than those for the ophthalmic applications. For instance, the ophthalmic aqueous pharmaceutical preparation of the present invention can widely be used for the treatment of inflammatory diseases such as rheumatism.

The ophthalmic aqueous pharmaceutical preparation of the present invention may, for instance, be prepared according to the following method. A desired amount of trometamol is dissolved in water by adding the same to hot water maintained at a temperature of 80° C. To the resulting trometamol solution, there is added meloxicam, followed by stirring the mixture while maintaining the whole of the aqueous mixture at 80° C. till the meloxicam is completely dissolved in the trometamol solution. The resulting aqueous solution is cooled down to room temperature and the volume of the aqueous solution is adjusted to a desired level by the addition of sterilized purified water. At this stage, it is possible to optionally add, to the aqueous solution, a variety of additives such as a pH-adjusting agent, a buffering agent, an isotonizing agent, a preservative and/or a stabilizing agent. Further the meloxicam-containing aqueous pharmaceutical preparation thus prepared is packed in a plastic eye drop bottle after sterilization of the pharmaceutical preparation through filtration to thus give a meloxicam-containing eye drop.

The ophthalmic aqueous pharmaceutical preparation of the present invention has a sufficient meloxicam concentration, is excellent in the anti-inflammatory effect, may be used as an eye drop since it is an aqueous pharmaceutical preparation and has a neutral pH value. The aqueous pharmaceutical preparation does not cause any separation of the effective component again and therefore, the preparation has a substantially weak irritating action to the eyes. Moreover, it is excellent in the storage stability.

Furthermore, the ophthalmic aqueous pharmaceutical preparation of the present invention is a non-steroidal drug. Therefore, it is never accompanied by any side effect even if it is administered for a long period of time and has a low probability of damaging corneal epithelial cells or the conjunctival cells.

DEST MODE FOR CARRYING OUT THE INVENTION

The present invention will hereunder be described in more detail with reference to the following working Examples, but the present invention is not restricted only to these specific examples at all.

EXAMPLE 1

(1) Preparation of Meloxicam Trometamol Salt

To one liter of distilled water, there were added 3.51 g (10 mM) of meloxicam and 1.21 g (10 mM) of trometamol and the mixture was heated to 80° C. to thus dissolve them, followed by the filtration of the resulting solution. The filtrate was concentrated under reduced pressure to a volume of 10 mL. After the crystals precipitated were filtered off, they were recrystallized from a mixed liquid comprising 20 mL of ethanol and 30 mL of hexane to give 3.02 g (yield 64%) of trometamol salt of meloxicam. The physical and chemical properties of the resulting meloxicam trometamol salt were found to be as follows:

Appearance: Yellow Needle Crystals
Melting point: 148–159° C. (decomposed)
Elemental Analysis: ($C_{18}H_{24}N_4O_7S_2$ (472.53))

|            | C (%) | H (%) | N (%) |
|------------|-------|-------|-------|
| Calculated | 45.75 | 5.12  | 11.86 |
| Found      | 45.80 | 4.88  | 11.69 |

MS (FAB): 473 ($M^+ + 1$)
$^1$H-NMR (δ ppm, in DMSO-$d_6$, Internal Standard: TMS): 2.30 (3H, s), 2.74 (3H, s), 3.27 (6H, s), 6.98 (1H, s), 7.56–7.73 (3H, m), 8.02 (1H, dd, J = 7.5, 1.3 Hz), 14.37 (1H, s)
$^{13}$C-NMR (δ ppm, in DMSO-$d_6$, Internal Standard: TMS): 11.1, 38.9, 59.6, 60.5, 107.6, 122.3, 123.6, 126.9, 129.9, 131.8, 134.2, 135.5, 135.9, 157.6, 163.2, 165.8
IR (KBr): 3352, 1620, 1514, 1462, 1396, 1330, 1168, 1067 $cm^{-1}$

EXAMPLE 2

(2) Preparation of Meloxicam Trometamol Salt

To 0.4 L of ethanol, there was added 2.42 g (20 mM) of trometamol and the resulting mixture was heated to 80° C. To the resulting trometamol solution, there was added 7.03 g (20 mM) of meloxicam and the resulting mixture was stirred for one hour, while maintaining the temperature of the mixture at 80° C. The solution was filtered while it was still hot, cooled to room temperature and then concentrated to dryness under reduced pressure. Cold ethanol (100 mL) was added to the resulting yellow solid residue and then the solid mass of the residue was triturated. The precipitates were subjected to suction filtration and the resulting crystalline powder was dried under reduced pressure to give 9.13 g (yield 97%) of meloxicam trometamol salt.

EXAMPLE 3

Comparison of Solubility

Sodium salt and meglumine salt of meloxicam were prepared according to the method disclosed in J.P. KOKAI No. Sho 54-92976.

These trometamol salt, sodium salt and meglumine salt of meloxicam were inspected for the solubility in water by the UV analysis and the results thus obtained were compared with one another. The results thus obtained are summarized in the following Table 1.

TABLE 1

| Salt | Solubility | | | |
|---|---|---|---|---|
| | Conversion into Salt (mg/mL) | Conversion into meloxicam (mg/mL) | pH | Remarks |
| Sodium Salt | 2.1 | 2.0 | 8.06 | Saturated Aqueous Solution (SAS) |
| Meglumine Salt | 3.6 | 2.3 | 8.57 | — |
| | 10.4 | 6.9 | 8.64 | — |
| | 30.4 | 19.5 | 8.73 | — |
| | 52.3 | 33.6 | 9.02 | SAS |
| Trometamol Salt | 12.0 | 8.9 | 7.52 | — |
| | 26.1 | 19.4 | 7.71 | — |
| | 60.1 | 44.7 | 7.93 | SAS |

The data shown in Table 1 clearly indicate that the trometamol salt of meloxicam has a maximum solubility (in water) on the order of 44.7 mg/mL as expressed in terms of the value converted into the amount of meloxicam and that the solubility value thereof is significantly higher than those observed for the other salts. The data also indicate that the solubility of meloxicam can be increased to not less than 20 times that observed for the sodium salt (solubility converted into the amount of meloxicam: 2.0 mg/mL) which has most commonly been used as a pharmaceutical agent by converting meloxicam into trometamol salt. Moreover, it is also proved that when the trometamol salt and meglumine salt are dissolved in water at the same concentration, the former is dissolved in water at a pH value in the proximity to the neutral level as compared with the latter.

EXAMPLES 4 to 5

To 95 mL of sterilized purified water, there was added 0.48 g or 0.41 g of trometamol, followed by dissolution thereof in water with stirring and then heating the aqueous solution to 70° C. To the aqueous solution, there was added 0.7 g of meloxicam and the resulting mixture was stirred for 2 hours to dissolve meloxicam while maintaining the temperature thereof at 70° C. After allowing the resulting solution to cool down to 25° C., the pH value thereof was adjusted to 8.4 using a 5N HCl solution or a 5N NaOH solution and sterilized purified water was added thereto to a total volume of 100 mL. The aqueous solution (20 mL) was charged into a 30 mL volume glass bottle equipped with a cap to give an aqueous pharmaceutical preparation of meloxicam.

Each aqueous pharmaceutical preparation of meloxicam thus prepared was stored at 25° C. for one hour to thus inspect the appearance of the preparation after the storage. The results thus obtained are listed in the following Table 2.

COMPARATIVE EXAMPLES 1 to 2

By way of comparison, the same procedures used in Example 4 were repeated except that the added amount of trometamol was changed to 0.36 g or that any trometamol was not added to thus prepare comparative meloxicam-containing pharmaceutical preparations. The appearances of these preparations were likewise observed in the same manner used in Example 4 and the results thus obtained are summarized in Table 2.

COMPARATIVE EXAMPLES 3 to 4

By way of comparison, the same procedures used in Example 4 were repeated except that the temperature of the aqueous solution in which trometamol had been dissolved was maintained at 30° C. or 50° C. to thus prepare comparative meloxicam-containing pharmaceutical preparations. The appearances of these preparations were likewise observed in the same manner used in Example 4 and the results thus obtained are summarized in Table 2.

COMPARATIVE EXAMPLES 5 to 7

By way of comparison, the same procedures used in Example 4 were repeated except that the added amount of meloxicam was changed to 0.5 g (Comparative Examples 5 and 6), that meglumine was added in an amount of 0.55 g (Comparative Examples 5 and 6) or 0.66 g (Comparative Example 7) instead of trometamol and that pH values were changed to 9.3 (Comparative Examples 5 and 7) and 8.4 (Comparative Example 6) to thus prepare comparative meloxicam-containing pharmaceutical preparations. The appearances of these preparations were likewise observed in the same manner used in Example 4 and the results thus obtained are summarized in Table 2.

COMPARATIVE EXAMPLES 8 to 9

By way of comparison, the same procedures used in Example 4 were repeated except that 0.24 g of monoethanolamine or 0.59 g of triethanolamine was substituted for the trometamol used in Example 4 to thus prepare comparative meloxicam-containing pharmaceutical preparations. The appearances of these preparations were likewise observed in the same manner used in Example 4 and the results thus obtained are summarized in Table 2.

TABLE 2

| | Example | | Comparative Example | | | | | | | | |
|---|---|---|---|---|---|---|---|---|---|---|---|
| | 4 | 5 | 1 | 2 | 3 | 4 | 5 | 6 | 7 | 8 | 9 |
| Meloxicam (w/v %) | 0.7 | 0.7 | 0.7 | 0.7 | 0.7 | 0.7 | 0.5 | 0.5 | 0.7 | 0.7 | 0.7 |
| Meglumine (w/v %) | | | | | | | 0.55 | 0.55 | 0.66 | — | — |
| (Molar Concn. Ratio to meloxicam) | | | | | | | (2.0) | (2.0) | (2.0) | — | — |
| Monoethanolamine (w/v %) | | | | | | | — | — | — | 0.24 | — |
| (Molar Concn. Ratio to meloxicam) | | | | | | | — | — | — | (2.0) | — |
| Triethanolamine (w/v %) | | | | | | | — | — | — | — | 0.59 |
| (Molar Concn. Ratio to meloxicam) | | | | | | | — | — | — | — | (2.0) |
| Trometamol (w/v %) | 0.48 | 0.41 | 0.36 | — | 0.48 | 0.48 | | | | | |
| (Molar Concn. Ratio to meloxicam) | (2.0) | (1.7) | (1.5) | — | (2.0) | (2.0) | | | | | |
| HCl/NaOH | q.s. | q.s. | q.s. | q.s. | q.s. | q.s. | q.s. | q.s. | q.s. | q.s. | q.s. |
| Temperature of Water (° C.) | 70 | 70 | 70 | 70 | 30 | 50 | 70 | 70 | 70 | 70 | 70 |
| pH | 8.4 | 8.4 | 8.4 | 8.4 | 8.4 | 8.4 | 9.3 | 8.4 | 9.3 | 8.4 | 8.4 |
| Appearance observed after the preparation | Yellow Trans. | Yellow Trans. | Susp. | Susp. | Susp. | Susp | Yellow Trans. | Susp. | Susp. | Susp. | Susp | q.s.: quantum sufficit
Yellow Trans.: yellow transparent
Susp.: suspension
Meloxicam MW = 351.41, Trometamol MW = 121.41, Ratio: 2.901
Meglumine MW = 193.98, Ratio: 1.812
Monoethanolamine MW = 61.08, Ratio: 5.753
Triethanolamine MW = 149.19, Ratio: 2.355

As will be seen from the data listed in Table 2, the meloxicam-containing aqueous pharmaceutical preparations prepared in Examples 4 and 5 do not cause any separation of meloxicam or they are aqueous pharmaceutical preparations in which meloxicam is completely dissolved. On the other hand, the results of Comparative Examples 1 to 2 indicate that if the molar concentration ratio of trometamol to meloxicam is less than 1.7 or the system is completely free of any trometamol, meloxicam is not completely dissolved in water and a suspension is formed.

The data obtained in Comparative Examples 3 to 4 indicate that if the temperature of the trometamol-containing aqueous solution is less than 70° C., meloxicam is not completely dissolved in water and a suspension is formed.

Further the data obtained in Comparative Examples 5 to 7 indicate that if meglumine is substituted for trometamol, 0.5% (w/v) of meloxicam is dissolved in water at pH 9.3, but the same amount of meloxicam is not completely dissolved in water at pH 8.4 although the contents of meloxicam and meglumine are identical to those used in the former (pH 9.3). In addition, these results also indicate that if the pH value is 9.3 and the concentration of meloxicam is 0.7% (w/v), meloxicam is not completely dissolved in water and a suspension is formed although the molar concentration ratio of meglumine to meloxicam is identical (2.0).

In addition, the data obtained in Comparative Examples 8 to 9 indicate that if triethanolamine or monoethanolamine is substituted for trometamol, 0.7% (w/v) of meloxicam is not completely dissolved in water although the molar concentration ratios of these compounds to meloxicam are identical to that of Example 4 in which trometamol is used.

EXAMPLES 6 to 10

Comparative Example 10

To 90 mL of sterilized purified water, there was added 0.34 g to 10 g of trometamol, followed by dissolution thereof with stirring and heating of the resulting aqueous solution to a temperature ranging from 70 to 90° C. To the heated aqueous trometamol solution, there was added 0.01 to 7 g of meloxicam and the meloxicam was dissolved in the aqueous solution with stirring the mixture for 2 hours while it was maintained at that temperature. The resulting aqueous solution was allowed to cool to a temperature of 25° C., a 5N HCl solution or a 5N NaOH solution was added thereto to adjust the pH value thereof to 7.0 to 9.0 and sterilized purified water was added to a total volume of 100 mL. Each resulting aqueous solution (20 mL) was charged into a lidded glass bottle having a volume of 30 mL to thus give each corresponding meloxicam-containing aqueous pharmaceutical preparation or comparative meloxicam-containing aqueous pharmaceutical preparation.

Each meloxicam-containing aqueous pharmaceutical preparation or comparative meloxicam-containing aqueous pharmaceutical preparation thus prepared was stored at 25° C. for one hour to thus inspect the appearance of the preparation after the storage. The results thus obtained are listed in the following Table 3.

TABLE 3

|  | Example | | | | | Comp. Ex. |
| --- | --- | --- | --- | --- | --- | --- |
|  | 6 | 7 | 8 | 9 | 10 | 10 |
| Meloxicam (w/v %) | 0.01 | 0.7 | 1 | 3 | 6 | 7 |
| Trometamol (w/v %) | 0.34 | 10 | 0.7 | 6 | 4.1 | 4.8 |
| Molar Concn. Ratio to meloxicam | 100 | 41 | 2.0 | 5.8 | 2.0 | 2.0 |
| HCl/NaOH | q.s. | q.s. | q.s. | q.s. | q.s. | q.s. |
| Temperature of Water (° C.) | 70 | 70 | 70 | 80 | 90 | 90 |
| pH | 7.0 | 9.0 | 8.0 | 8.0 | 8.0 | 8.0 |
| Appearance observed after the preparation | Yellow Trans. | Yellow Trans. | Yellow Trans. | Yellow Trans. | Yellow Trans. | Susp |

The meloxicam-containing aqueous pharmaceutical preparations prepared in Examples 6 to 10 were free of any separation of meloxicam and were thus aqueous pharmaceutical preparations in which meloxicam was completely dissolved. On the other hand, the results obtained in Comparative Example 10 clearly indicate that if the meloxicam concentration exceeds 6% (w/v), meloxicam is not completely dissolved in water and a suspension is formed although the molar concentration ratio of trometamol to meloxicam is identical to that used in Example 10.

Formulation 1

To 900 mL of sterilized purified water, there was added 11 g of trometamol, followed by dissolution thereof with stirring and heating of the aqueous solution to a temperature ranging from 70 to 90° C. To the resulting aqueous solution, there was added 15 g of meloxicam and it was dissolved in the aqueous solution with stirring for 2 hours, while the mixture was maintained at that temperature. The resulting aqueous meloxicam-containing solution was allowed to cool to 25° C., followed by addition of 0.05 g of benzalkonium chloride, 0.05 g of EDTA.2Na and 13 g of glycerin and mixing of these components with stirring till all of the components were completely uniformly dissolved. The pH value of the solution was adjusted to 8.0 by addition of a 1N hydrochloric acid solution and sterilized purified water was added to the solution to a total volume of one liter. This aqueous solution was sterilized by filtration thereof through a membrane filter having a pore size of 0.22 μm and then charged into a 5 mL volume plastic eye drop bottle to give a meloxicam-containing aqueous eye drop.

| <Eye Drop> | |
| --- | --- |
| Meloxicam | 1.5% (w/v) |
| Trometamol | 1.1% (w/v) |
| Benzalkonium Chloride | 0.005% (w/v) |
| EDTA · 2Na | 0.005% (w/v) |
| Glycerin | 1.3% (w/v) |
| Hydrochloric Acid Solution | q.s. |
| Sterilized Purified Water | to 1 L |

Formulation 2

To 900 mL of sterilized purified water, there was added 7 g of trometamol, followed by dissolution thereof with stirring and heating of the aqueous solution to a temperature ranging from 70 to 90° C. To the resulting aqueous solution, there was added 10 g of meloxicam and it was dissolved in the aqueous solution with stirring for 2 hours, while the mixture was maintained at that temperature. The resulting aqueous meloxicam-containing solution was allowed to cool to 25° C., the pH value thereof was adjusted to 8.3 by the addition of a 1N HCl solution and sterilized purified water was added to the solution to a total volume of one liter. This aqueous solution was sterilized by filtration thereof through a membrane filter having a pore size of 0.22 μm and then charged into a 1 mL volume glass ampoule, followed by closing through fusion to thus give a meloxicam-containing aqueous injection.

| <Aqueous Injection> | |
| --- | --- |
| Meloxicam | 1% (w/v) |
| Trometamol | 0.7% (w/v) |
| Hydrochloric Acid Solution | q.s. |
| Sterilized Purified Water | to 1 L |

Formulation 3

After 80 mL of sterilized purified water was heated to 70° C., 1.0 g of borax, 1.0 g of propylene glycol and 1.0 g of polyvinyl pyrrolidone K25 (Koridon™ 25 available from BASF Company) were added to and dissolved in the heated water. Then 1.36 g (1.0 g as expressed in terms of the amount of meloxicam) of trometamol salt of meloxicam prepared according to the method described in Example 1 was added to and dissolved in the resulting solution, while maintaining the temperature of the solution at 70° C . The resulting aqueous meloxicam-containing solution was allowed to cool to room temperature, the pH value thereof was adjusted to 8.0 by the addition of a 3N HCl solution and sterilized purified water was added to the solution to a total volume of 100 mL to thus give a meloxicam trometamol salt-containing eye drop.

| <Eye Drop> | |
| --- | --- |
| Meloxicam Trometamol Salt | 1.36% (w/v) (1.0% (w/v) as expressed in terms of the amt. of meloxicam) |
| Borax | 1.0% w/v |
| Propylene Glycol | 1.0% (w/v) |

-continued

| <Eye Drop> | |
|---|---|
| Polyvinyl Pyrrolidone K25 | 1.0% (w/v) |
| Hydrochloric Acid Solution | q.s. |
| Sterilized Purified Water | to 100 mL |

The eye drop thus prepared was charged into a glass bottle, sealed with a cap and the glass bottle was stored in a thermostatic chamber at 25° C. for 6 months.

The eye drop immediately after the preparation was a yellow transparent aqueous solution. Foreign substance such as precipitates were not formed at all even after the storage at 25° C. for 6 months. In addition, the eye drop was inspected for any change in the content of meloxicam by the HPLC technique and it was found that the meloxicam content observed after the storage at 25° C. for 6 months was 98.2% relative to that observed when the storage was initiated.

The foregoing clearly indicates that the eye drop containing the meloxicam trometamol salt is a quite stable one since it is free of any separation of meloxicam crystal and any reduction of the meloxicam content.

INDUSTRIAL APPLICABILITY

The ophthalmic aqueous pharmaceutical preparation of the present invention comprises meloxicam as a hardly soluble drug dissolved in water having a pH value falling within the neutral region, does not give a stimulus to a patient upon the administration thereof, it has no apprehension of uncomfortable feeling with foreign substances (or suspensoids) upon the administration thereof, the scattering of dose and the adhesion of the suspended matter or suspensoids to the container of the suspension, which are disadvantages associated with the conventional suspensions. Moreover, the pharmaceutical preparation of the invention is excellent in the anti-inflammatory effect and thus can effectively be used in the treatment of symptoms such as conjunctivitis. In addition the preparation is also excellent in the safety and storage stability.

What is claimed is:

1. An ophthalmic aqueous pharmaceutical preparation comprising meloxicam and trometamol, wherein the molar concentration of trometamol ranges from 1.7 to 100 times that of meloxicam.

2. The ophthalmic aqueous pharmaceutical preparation of claim 1, wherein the concentration of meloxicam ranges from 0.01 to 6% (w/v).

3. The ophthalmic aqueous pharmaceutical preparation of claim 1, wherein the concentration of meloxicam ranges from 0.7 to 3% (w/v) and the concentration of trometamol ranges from 0.48 to 6% (w/v).

4. The ophthalmic aqueous pharmaceutical preparation of claim 1, wherein the pH value of the preparation ranges from 7 to 9.

5. The ophthalmic aqueous pharmaceutical preparation of claim 1, wherein said preparation is prepared by dissolving meloxicam in an aqueous trometamol solution at a high temperature.

6. The ophthalmic aqueous pharmaceutical preparation of claim 5, wherein the high temperature is from 70 to 100° C.

7. An ophthalmic aqueous pharmaceutical solution as claimed in claim 1, wherein the solution is stable at 25° C. for at least 6 months.

* * * * *

UNITED STATES PATENT AND TRADEMARK OFFICE
CERTIFICATE OF CORRECTION

| | | |
|---|---|---|
| PATENT NO. | : 7,105,512 B2 | Page 1 of 1 |
| APPLICATION NO. | : 10/153632 | |
| DATED | : September 12, 2006 | |
| INVENTOR(S) | : Daisuke Morizono et al. | |

It is certified that error appears in the above-identified patent and that said Letters Patent is hereby corrected as shown below:

On the title page, Item 63, please insert the Related U.S. Application Data. Item 63 should read:

--Related U.S. Application Data:
(63) Continuation of application No. PCT/JP00/08227, filed on Nov. 22, 2000.--

Signed and Sealed this

Nineteenth Day of December, 2006

JON W. DUDAS
*Director of the United States Patent and Trademark Office*